(12) United States Patent
Guth et al.

(10) Patent No.: US 8,524,701 B2
(45) Date of Patent: *Sep. 3, 2013

(54) USE OF A SPECIFIC CYCLIC AMINE DERIVATIVE OR THE PHARMACEUTICALLY ACCEPTABLE SALTS THEREOF FOR THE TREATMENT OR PREVENTION OF HEART FAILURE

(75) Inventors: Brian Guth, Warthausen (DE); Randolph Seidler, Sandy Hook, CT (US); Juergen Daemmgen, Ochsenhausen (DE)

(73) Assignee: Boehringer Ingelheim Pharma GmbH & Co. KG (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/139,091

(22) Filed: Jun. 13, 2008

(65) Prior Publication Data

US 2008/0312210 A1  Dec. 18, 2008

Related U.S. Application Data

(63) Continuation of application No. 11/627,374, filed on Jan. 25, 2007, now abandoned, which is a continuation of application No. 11/273,221, filed on Nov. 14, 2005, now abandoned, which is a continuation of application No. 10/626,138, filed on Jul. 24, 2003, now abandoned.

(60) Provisional application No. 60/405,915, filed on Aug. 26, 2002.

(30) Foreign Application Priority Data

Jul. 25, 2002  (EP) ..................................... 02016602

(51) Int. Cl.
*A61K 31/195* (2006.01)
*A61K 31/55* (2006.01)
*A61K 45/06* (2006.01)

(52) U.S. Cl.
USPC ............ 514/212.04; 514/212.06; 514/212.07; 514/542

(58) Field of Classification Search
USPC .................. 514/26, 212.06, 212.07, 542, 546
See application file for complete search history.

(56) References Cited

U.S. PATENT DOCUMENTS 5,175,157 A   12/1992  Psiorz et al.
5,296,482 A    3/1994  Peglion et al.
(Continued)

FOREIGN PATENT DOCUMENTS

CA   1321194 C     8/1993
CA   2 435 526 A1  1/2004
(Continued)

OTHER PUBLICATIONS

Rieu et al, Eur. J. Med. Chem., 1993, 28, 683-691.*
(Continued)

*Primary Examiner* — Shaojia Anna Jiang
*Assistant Examiner* — Ganapathy Krishnan
(74) *Attorney, Agent, or Firm* — Michael P. Morris; Wendy M. Gombert

(57) ABSTRACT

The present invention provides the use in a pharmaceutical composition of a specific cyclic amine derivative, or its pharmaceutically acceptable salts, for the treatment of heart failure of any aetiology.

12 Claims, 4 Drawing Sheets

(56) References Cited

U.S. PATENT DOCUMENTS

| | | | |
|---|---|---|---|
| 5,308,853 A | 5/1994 | Hodges et al. | |
| 5,516,773 A | 5/1996 | Rose | |
| 5,595,987 A | 1/1997 | Lasker et al. | |
| 5,721,217 A * | 2/1998 | Liu et al. | 514/26 |
| 5,968,978 A * | 10/1999 | Kleemann et al. | 514/524 |
| 6,083,991 A * | 7/2000 | Bergeron, Jr. | 514/646 |
| 6,204,281 B1 | 3/2001 | Webb et al. | |
| 6,395,728 B2 | 5/2002 | Webb et al. | |
| 6,573,279 B1 | 6/2003 | Watanabe et al. | |
| 7,208,508 B2 * | 4/2007 | Daemmgen et al. | 514/355 |
| 2004/0014795 A1 | 1/2004 | Daemmgen et al. | |
| 2004/0138306 A1 | 7/2004 | Guth et al. | |
| 2006/0063840 A1 | 3/2006 | Guth et al. | |
| 2006/0100278 A1 | 5/2006 | Cooper et al. | |
| 2007/0142354 A1 | 6/2007 | Guth et al. | |
| 2008/0312210 A1 | 12/2008 | Guth et al. | |

FOREIGN PATENT DOCUMENTS

| | | |
|---|---|---|
| EP | 0224794 A2 | 6/1987 |
| EP | 0330052 A2 | 8/1989 |
| EP | 0471388 A2 | 2/1992 |
| JP | 2000-355577 A | 12/2000 |
| JP | 2004-264195 A | 9/2004 |
| RU | 2078536 C1 | 5/1997 |
| WO | 00/02543 A2 | 1/2000 |
| WO | 00/75133 A1 | 12/2000 |
| WO | 01/78699 A2 | 10/2001 |
| WO | 2004011006 A1 | 2/2004 |

OTHER PUBLICATIONS

The Merck Manual, 1987, Fifteenth Edition, pp. 519-521.*
J.P. Rieu, et al; Synthesis and Bradycardic Activity of a Series of Substituted 3-Aminoalky1-2,3-Dihydro-4H-1,3-Benzoxazin-4-ones as Potent Antiischemics; Eur. Journal Med. Chem. (1993) vol. 28 pp. 683-691.
Shinke, T. et al; Beneficial Effects of Heart Rate Reduction on Cardiac Mechanis and Energetics in Patients with Left Ventricular Dysfunction; Japanese Circulation Journal; 1999; 957-964; vol. 63.
The Merck Manual, 1987, 15th Edition, pp. 519-522.
Merck Index, 12th Edition, 1996, pp. 541 and 1696.
Granetzny, A., et al. "Pharmacologic heart rate reduction: effect of a novel specific bradyardic agent on the heart," The Thoracic and Cardiovascular Surgeon, vol. 46, 1998, pp. 63-69.
Lijnen, P. and Petrov, V: Renin-Angiotensin System, Hpertrophy and Gene Expression in Cardiac Myocytes; J. Mol Cell Cardiol, 31, pp. 949-970 (1999).
P. Gregor, et al; Use of Verapamil in the Treatment of Hypertrophic Cardiomyopathy, Cor Et Vasa, Bd. 28 Nr. 6, 1986, pp. 404-412, XP 001024692.
A. Hartmann, et al; Persisting effect of Calcium-channel blockers on the left ventricular function in hypertrophic cardiomyopathy after 14 years' treatment, Angiology, Bd. 47, Nr. 8, 1996 pp. 765-773—XP 001024817.
H. Toshima, et al; Comparable effects of oral diltiazem and verapamil in the treatment of hypertrophic cardiomyopathy, Japanese Heart Journal, Bd. 27, Nr. 5, 1986 pp. 701-715, XP0010214687.
G. Kober, et al; Clinical cardiology hypertrophic cardiomyopathy. Long-term verapamil versus propranolol treatment of hypertrophic cardiomyopathy in matched pairs of patients.
Circulation Supplement, Abstracts from the 60th Scientific Session Bd. 76, Nr. 4, 1987 p. IV-248—XP001024696.
S.E. Epstein, et al; Verapamil; Its potential for causing serious complications in patients with hypertrophic cardiomyopathy; Circulation, Bd. 64, Nr. 3, 1981, pp. 437-441 XP001024694.
Database WPI, Section PQ, Week 199747 Derwent Publications Ltd. London, GB; Class P31; AN 1997-510672, XP 002179143.
The Extra Pharmacopoeia, 30th Edition, The Pharmaceutical Press, London, XP 002179142, p. 668.
D.P. Nichols, et al; Cardio Vascular effects of Alinidine and Propranolol alone and in combination with Hydralazine in Normal Man, Br. J. Clin. Pharmacol, (1983) 15 (1), 21-30-XP001041903.

Muller, C. A. et. al.; Combination of a Calcium Antagonist, Verapamil, with an Angiotensin Converting Enzyme Inhibitor, Trandolapril, in Experimental Myocardial Ischemia and Reperfusion; Antiarrhythmic and Hemodynamic Effects of Chronic Oral Pretreatment); Cardiovascular Drugs and Therapy 1998; 12:449-455;Kluwer Academic Publishers, Boston.
Ruschitzka, F.T., et. al.: Combination of Ace Inhibitors and Calcium Antagonists: A logical approach;J Cardiovasc Pharmacol, vol. 31 Supplement 2,1998, pp. S5-S16.
Goodman & Gilman's: The Pharmacological Basis of Therapeutics, 10th edition, McGraw-Hill Medical Publishing Division, 2001, pp. 54-56.
Daemmgen, J., et al. "Method for improving diagnostic quality in echocardiography", U.S. Appl. No. 11/470,303, filed Sep. 6, 2006.
Arnold M. Katz; Maladaptive Growth in the Failing Heart: the Cardiomyopathy of Overload; Cardiovascular Drugs and Therapy (2002) vol. 16, No. 3 pp. 245-249.
Barry J. Maron; Hypertrophic Cardiomyopathy, A Systematic Review; JAMA (2002) vol. 287, No. 3 pp. 1308-1320.
Cervetto, L. et al., "Effects of blocking the rod hyperpolarization activated current on the flash ERG". Investigative Ophthalmology and Visual Science, Feb. 15, 1996, vol. 37, No. 3, S347, 1598-B501.
Ragueneau, I. et al., "Pharmacokinetic-pharmacodynamic modling of the effects of ivabradine, a direct sinus node inhibitor, on heart rate in healthy volunteers". Clinical Pharmacology, 1998, vol. 64 (2), pp. 192-203.
Raes, A. et al., "Use-dependent block of Ih in mouse dosal root ganglion neurons by sinus node inhibitors". British Journal of Pharmacology, 1998, vol. 125, pp. 741-750.
Pape, H.C., "Specific bradycardic agents block the hyperpolarization-activated cation current in central neurons". Neuroscience, vol. 59, No. 2, pp. 363-373, 1994.
Abstract in English for JP2000355577, Dec. 26, 2000.
Abstract in English for JP2004264195, Sep. 24, 2004.
Abstract in English for RU2078536, May 10, 1997, Derwent.
Abstract in English of EP0330052, Aug. 30, 1989.
Berkow et al., "Hypertrophic Cardiomyopathy". The Merck Manual of Diagnosis and Therapy, Fifteenth Edition, Chapter 27, Merck Sharp & Dohme Research Laboratories, Rahway, NJ, 1987, pp. 519-522.
Friart et al., "Doppler evaluation of left ventricular filling: effect of verapamil on non-obstructive hypertrophic cardiomyopathy". European Heart Journal, vol. 11, No. 9, 1990, pp. 839-844.
Harrison et al., "Use of Exercise Doppler Echocardiography to Evaluate Cardiac Drugs: Effects of Propranolol and Verapamil on Aortic Blood Flow Velocity and Acceleration". Journal of the American College of Cardiology, vol. 11, No. 5, May 1988, pp. 1002-1009.
Hassager et al., "Different Effects of Calcium Antagonist and Beta-Blocker Therapy on Left-Ventricular Diastolic Function in Ischemic Heart Disease". Cardiology, vol. 96, No. 2, 2001, pp. 65-71.
Ilgenli et al., "Bisoprolol Improves Echocardiographic Parameters of Left Ventricular Diastolic Function in Patients with Systemic Hypertension". Cardiology, vol. 106, No. 3, 2006, pp. 127-131.
International Search Report and Written Opinion for PCT/EP2003/07929 mailed Oct. 9, 2003.
Kober et al., "Clinical Cardiology: Hypertrophic Cardiomyopathy; Tuesday Afternoon; Long-Term Verapamil vs Propranolol Treatment of Hypertrophic Cardiomyophathy in Matched Pairs of Patients". Circulation, Abstracts, vol. 76, Supp IV, Oct. 1987, p. IV-248.
Lei et al., "Bradycardia induces angiogenesis, increases coronary reserve, and preserves function of the postinfarcted heart". Circulation: Journal of the American Heart Association, vol. 110, Aug. 2004, pp. 796-802.
Manca et al., "Doppler Evaluation of Left Ventricular Filling: Effect of Atenolol in Patients with Hypertension". Current Therapeutic Research, vol. 51, No. 3, 1992, pp. 334-341.
Myreng et al., "Effects of verapamil on left ventricular relaxation and filling dynamics in coronary artery disease: A study by pulsed Doppler echocardiography". American Heart Journal, vol. 117, No. 4, Apr. 1989, pp. 870-875.

Osipov et al., "Study of hemodynamic effects of allapinin and metoprolol using continuous wave Doppler echocardiography at rest and during physical exercise in patients with paroxysmal supraventricular tachycardia". Kardiologiia, vol. 31, No. 8, Aug. 1991, pp. 83-86. [Abstract Only, Medline].

Vanhees et al., "Influence of $\beta^1$- Versus $\beta^2$-Adrenoceptor Bloackade on Left Ventricular Function in Humans". Journal of Cardiovascular Pharmacology, vol. 8, No. 5, 1986, pp. 1086-1091.

Wakita et al., "The relationship between the improvement of cardiac function and the myocardial uptake of I-123 metaiodobenzylguanidine in patients with dilated cardiomyopathy treated by beta-blocker". Journal of Cardiology, vol. 26, No. 3, Sep. 1995, pp. 177-183. [Abstract Only, Medline].

* cited by examiner

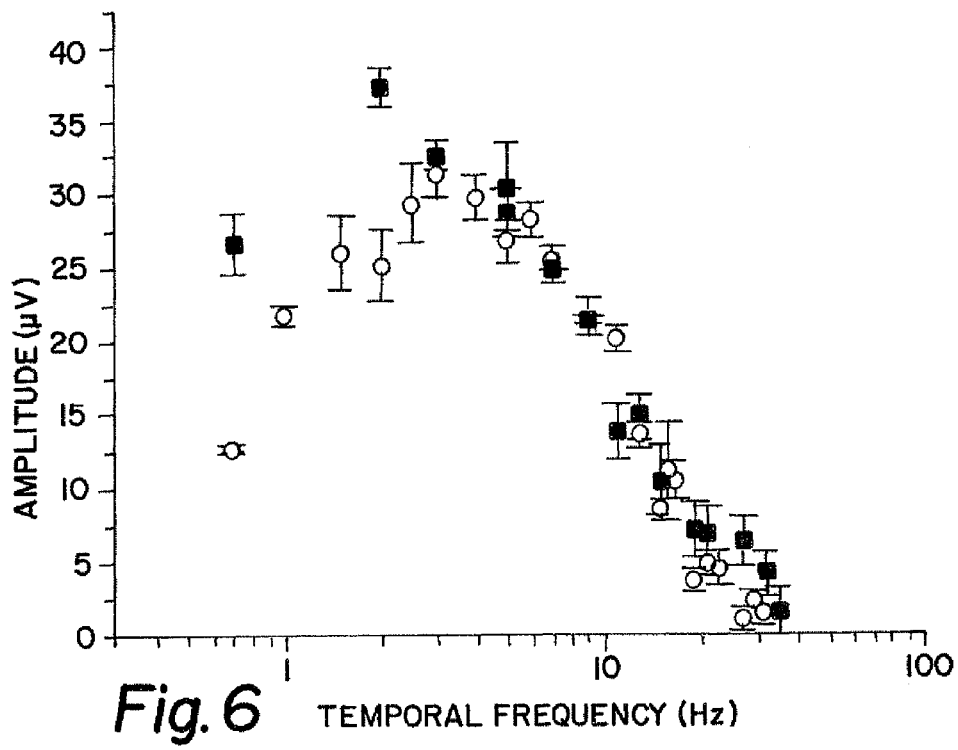
Fig. 6 TEMPORAL FREQUENCY (Hz)
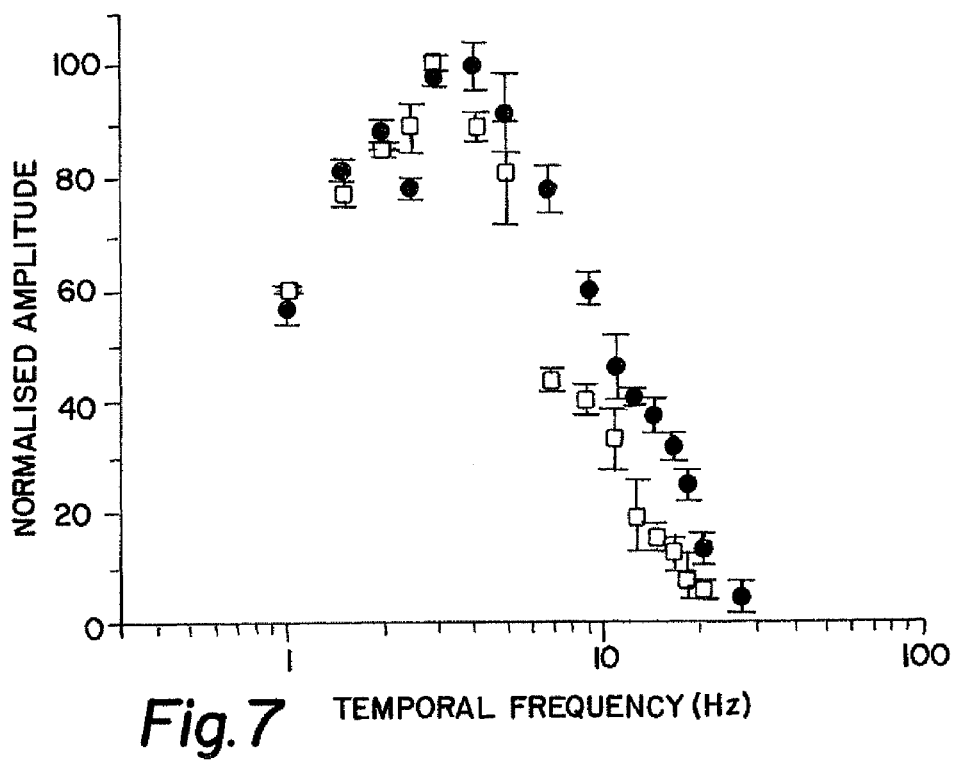
Fig. 7 TEMPORAL FREQUENCY (Hz)

USE OF A SPECIFIC CYCLIC AMINE DERIVATIVE OR THE PHARMACEUTICALLY ACCEPTABLE SALTS THEREOF FOR THE TREATMENT OR PREVENTION OF HEART FAILURE

RELATED APPLICATIONS

The present application is a continuation of U.S. patent application Ser. No. 11/273,221 filed on Nov. 14, 2005, which is a continuation of U.S. patent application Ser. No. 10/626,138 filed on Jul. 24, 2003, which claims priority of U.S. Provisional Pat. App. No. 60/405,915 filed on Aug. 26, 2002 and EP 02 016 602 filed on Jul. 25, 2002, all of which are incorporated by reference herein.

FIELD OF THE INVENTION

The present invention relates to the novel use of a cyclic amine derivative, namely cilobradine, or the pharmaceutically acceptable salts thereof, for the treatment or prevention of heart failure of any aetiology.

BACKGROUND OF THE INVENTION

Heart failure is a major world-wide public health problem and is the only cardiac disorder that is increasing in incidence. In the United States alone, 5 million patients suffer from heart failure, with a new diagnosis made in 0.5 million patients per year. Despite advances in therapy over the last decade, the annual number of hospitalisations has increased from 550 000 to 900 000 as a primary diagnosis, and from 1.7 to 2.6 million as a primary or secondary diagnosis (J. Am. Pharm. Assoc., vol. 41(5), pp. 672-681, 2001). Unless treated, heart failure may lead to death. Hence, new approaches are warranted to treat or prevent heart failure.

Although the terminology heart failure seems to be the most accepted terminology for describing this cardiac disorder, various further equivalent terminologies can be found in the scientific, patent or medical literature as, for example, cardiac failure, insufficient cardiac output, cardiac insufficiency, cardiac collapse and cardiac syncope.

Furthermore, though heart failure is invariably a chronic cardiac disorder, often with an insidious onset, heart failure may be present acutely or be punctuated by episodes of acute deterioration, so called "decompensated" heart failure. To describe these conditions also related to heart failure, further terminologies will commonly be found in the scientific, patent or medical literature such as, for example, chronic heart failure, acute heart failure, heart decompensation, cardiac decompensation and cardial decompensation.

Lastly, as will be explained in the foregoing, as heart failure can be caused by a dysfunctioning of the heart reflected by various clinical presentations and sometimes subjected to further complications, further terminologies related to heart failure will also commonly be found in the scientific, patent or medical literature such as, for example, myocardial failure, myocardial insufficiency, heart muscle insufficiency, cardiac muscle insufficiency, heart muscle weakness, cardiac muscle weakness, systolic or left ventricular heart failure, diastolic heart failure, left or right sided heart failure, biventricular heart failure and congestive heart failure.

Hence, a distinction can be made between the systolic or diastolic origin of the dysfunctioning. Commonly, heart failure is a consequence of a progressive deterioration of myocardial contractile function, named systolic or left ventricular dysfunction. However, diastolic dysfunction is becoming increasingly recognised as an important cause of heart failure too. This occurs when the heart chambers are unable to expand sufficiently during diastole (period of heart relaxation in which the chambers fill with blood) and hence blood volume in the ventricles is inadequate. Whether systolic and/or diastolic dysfunction is the basis of heart failure, cardiac output is diminished. When additionally there is "damming" back of blood in the venous system, congestion may ensue in the lungs (pulmonary oedema) and/or in the abdomen or peripheries (peripheral oedema). When both occur, the terminology congestive heart failure is often used.

In other respects, the distinction between left and right sided heart failure can be applied to reflect the clinical presentation (i.e. pulmonary oedema indicative of left sided heart failure, whereas the principal symptom of right sided heart failure is fluid retention in the peripheries) or to denote the underlying cause. Right sided heart failure is most commonly a consequence of left sided heart failure, although diseases of the lung (such as chronic obstructive pulmonary disease), the right ventricle (e.g. right ventricular infarction) or the vasculature (primary or secondary pulmonary hypertension, the latter due to conditions such as pulmonary embolism for example), may result in predominate right sided heart failure.

According to the International Classification of Functioning, Disability and Health, lastly published by the World Health Organization on 15 Nov. 2001 (ISBN 91 4 1545429) and accepted by 191 countries during the $54^{th}$ World Health Assembly (Resolution WHA 54.21), heart failure occurs when the heart function of pumping the blood in adequate or required amounts and pressure throughout the body is impaired.

As cardiac output is normally 5 liters/minute, although this can increase five fold with heavy exercise, in essence, heart failure occurs when the heart is unable to meet this demand.

As heart failure manifests itself in a variety of ways, at the time of this patent application, the treatment or prevention of heart failure comprises a combination of typical medications. These medications are based upon the principles of promoting fluid excretion to lessen oedema and volume overload (e.g. various types of diuretics), vasodilatory drugs to reduce preload (i.e. atrial pressures) and/or afterload (i.e. pressure against which the heart has to beat), and inotropic drugs to increase contractility.

Vasodilatory drugs available at this time include Angiotensin Converting Enzyme (ACE) inhibitors, Angiotensin II Receptor blockers (ARBs) and nitrate venodilators. Inotropic drugs are usually administered only in acute situations Although cardiac glycosides such as digoxin are sometimes prescribed for their inotropic properties, their use is more common in heart failure patients when atrial arrhythmias co-exist.

Recently, beta-blockers, which were once thought to be contra-indicated in heart failure due to their negative inotropic (decreased contractility) property, have been shown to be effective in the treatment of heart failure. Meta-analyses of randomised controlled trials have shown that, in addition to established background therapy of ACE inhibitors and diuretics with or without digoxin, a reduction of all cause mortality and cardiovascular morbidity is conferred by beta-blockers such as carvedilol, metoprolol or bisoprolol (Brophy J. M. et al., Ann. Intern. Med. 2001, Vol. 134, pp. 550-560; Lechat P. et al., Circ. 1998, pp. 1184-1191; Heidenreich P. A. et al., J. Am. Coll. Cardiol., 1997, Vol. 30, pp 27-34).

As heart failure progresses, heart failure treatment is also usually not limited to one single therapy. Hence, add-on therapy use is disclosed for carvedilol, for example, in WO 96/24348, for decreasing the mortality of patients suffering from congestive heart failure. WO 96/40258 discloses a combination therapy comprising an angiotensin II antagonist and spironolactone, an aldosterone receptor antagonist, for the treatment of hypertension, congestive heart disease, cirrhosis and ascites. WO 00/02543 discloses a combination therapy comprising an angiotensin II antagonist (valsartan) and a calcium channel blocker (amlodipine or verapamil) for the treatment of several heart diseases, amongst which acute and chronic congestive heart diseases are cited.

However, as with all therapies, there are constraints to their use. For example, beta-blockers may be contra-indicated in patients with concomitant diseases such as asthma, peripheral vascular disease and decompensated heart failure. Certain drug classes may not be tolerated due to unwanted side effects, e.g. cough with ACE inhibitors, fatigue, dizziness or impotence in association with beta-blockers, and hyponatremia with diuretics. Furthermore, a slow and careful titration period may be required upon drug initiation, as with beta-blockers, where if not performed, the initial negative effects on the heart's pumping action (negative inotropy) may result in drug intolerance and deterioration in heart failure status.

Hence, to echo the statement set out at the beginning of this section, despite the advances made by therapies established at this time, there is still a need to reduce the unacceptable burden of heart failure and new additional approaches to treatment and prevention of disease progression should be sought.

In searching for new therapies for heart failure, the underlying pathophysiology of the failing heart needs to be considered. It has long been observed in the failing heart that heart rate and contractility are initially increased in order to maintain cardiac performance. In the long term, this response is ultimately damaging. It is, for example, acknowledged that increased heart rate is a risk factor for mortality and morbidity with adverse consequences on vascular function, atherogenesis, myocardial ischaemia, myocardial energetics and left ventricular function. Chronic tachyarrhythmias are a cause of reversible cardiomyopathy in humans and rapid atrial pacing is established as an animal model of cardiomyopathy. In chronic heart failure, excess adrenergic stimulation signals adverse biological responses (including increased heart rate) via $\beta 1$, $\beta 2$ and $\alpha 2$ receptors in the myocardium.

In the failing heart, maintenance of adequate ventricular contraction is sought, but occurs at the expense of oxygen and energy consumption by the myocardium. Heart rate influences such energy demand, with increased heart rate requiring greater expenditure of energy. Thus, greater energetic efficiency could potentially result if heart rate were lowered in heart failure patients.

It thus follows that drugs which have the ability to reduce heart rate may be of benefit in the treatment or prevention of heart failure. For the treatment of cardiac insufficiency, a term also used to denote heart failure, EP 0 471 388 (and its US counterpart U.S. Pat. No. 5,516,773) suggests the use of a specific group of compounds derived from the benzazepine basic chemical structure, and more specifically the compound named zatebradine [1-(7,8-dimethoxy-1,3,4,5-tetrahydro-2H-3-benzazepin-2-one-3-yl)-3-[N-methyl-N-(2-(3,4-dimethoxy-phenyl)-ethyl)-propane].

These benzazepine derivatives were firstly described in EP 0 065 229, as well as their ability to reduce heart rate (bradycardic effect) by acting directly on the sinoatrial node, and their ability to reduce the oxygen requirement of the heart. Zatebradine is also known from WO 01/78699 for the treatment and induction of the regression of idiopathic hypertrophic cardiomyopathy (HCM), ischemic cardiomyopathy and valvular hypertrophic heart diseases.

The effects of the bradycardic agent zatebradine have been studied in a small number of patients with heart failure, also subject to no therapy or atrial pacing, to induce a tachycardia (Shinke et al., Jpn. Circ. Journal, 1999, Vol. 63, pp. 957-964) or in comparison to the beta-blocker propranolol (Shinke et al. Abstract Circ., 1997, Vol. 96, I-644).

In the former study, it was concluded by the authors that the oxygen saving effect of the bradycardia due to zatebradine treatment could be beneficial for the treatment of heart failure. In the latter study, the comparable heart rate reduction observed with zatebradine and the beta-blocker had favourable effects compared to pre-treatment. However, it should be noted that under beta-blocker treatment overall cardiac efficiency was preserved, since the energy saving benefits of heart rate reduction remedied the observed negative effect on contractility. This, the authors proposed, might account for good beta-blockers tolerance and possible efficacy in heart failure. Zatebradine treatment however improved cardiac efficiency since heart rate reduction occurred, but with no accompanying adverse effect on contractility.

It should be noted that these two studies are small and do not attempt to evaluate the benefits of chronic zatebradine administration on the hemodynamic or clinical manifestations of heart failure. Furthermore, the relationships between heart rate reduction, left ventricular function and prognosis in heart failure are complex. However, there is a scientific rationale that improved cardiac energetics secondary to heart rate reduction is an important concept in the treatment and prevention of the progression of heart failure due to systolic and/or diastolic dysfunction (Laperche et al., Heart 1999, Vol. 81, pp. 336-341).

Another specific group of compounds derived from a basic cyclic amine chemical structure, have been shown to also have valuable pharmacological bradycardic properties. These compounds, the process for their preparation and pharmaceutical compositions containing them are described in EP 0 224 794 and its US counterpart U.S. Pat. No. 5,175,157.

One of these cyclic amine derivatives, 3-[(N-(2-(3,4-dimethoxy-phenyl)-ethyl)-piperidin-3-yl)-methyl]-7,8-dimethoxy-1,3,4,5-tetrahydro-2H-3-benzazepin-2-one, and more particularly its S-(+) enantiomer named cilobradine [(+)-3-[(N-(2-(3,4-dimethoxy-phenyl)-ethyl)-piperidin-3-(S)-yl)-methyl]-7,8-dimethoxy-1,3,4,5-tetrahydro-2H-3-benzazepin-2-one], is also known from WO 01/78699 for the treatment and induction of the regression of idiopathic hypertrophic cardiomyopathy (HCM), ischemic cardiomyopathy and valvular hypertrophic heart diseases.

However, these cyclic amine derivatives, and more specifically cilobradine, have not been suggested for the treatment or prevention of heart failure.

Scientific studies performed with zatebradine and cilobradine in order to determine the mechanism of action of these bradycardic substances have shown that both zatebradine and cilobradine selectively block hyperpolarisation activated, cAMP-modulated cation current channels (HCN) in cardiac conductive tissue, channels responsible for the transmembrane current known as $I_f$. It is through blockade of this current that zatebradine and cilobradine are assumed to produce their specific bradycardic effect.

However, HCN channels are widely distributed in the nervous system, and in the eye they mediate the current known as $I_h$. The effect of zatebradine and cilobradine on the $I_h$ channel has also been investigated (Neuroscience, Vol. 59(2), pp. 363-373, 1994 for zatebradine, and British Journal of Pharmacology, Vol. 125, pp. 741-750, 1998 for cilobradine). The results have suggested that although $I_h$ can also be blocked by these compounds, the interaction with the channels is somewhat different for both tissues. Since $I_h$ has been described in the different neurones of the visual signal processing system, the effect on $I_h$ current has been suggested to be an explanation for the side-effects (visual disturbances) seen by patients treated with $I_f$-blockers.

Further studies have been performed using electroretinogram (ERG) responses recorded from cat eyes and psychophysical measurements conducted on volunteer human subjects, in normal conditions and after administration of zatebradine (Archives Italiennes de Biologie, vol. 137, pp. 299-309, 1999, and Vision Research, vol. 39, pp. 1767-1774, 1999). The results of these studies have shown that zatebradine reduces the amplitude of the response to stimuli of frequency above 1 Hz, as shown by the ERG recordings. Furthermore, the measurement of the attenuation and phase characteristics of the first harmonic constructed by plotting the response amplitude and the phase as a function of the temporal frequency of the stimulus in control conditions and after intravenous injection or oral administration of zatebradine have shown that the main effect of the $I_h$ blocker zatebradine is to decrease the response amplitude to stimuli in the frequency range of 2 to 15 Hertz, by introducing a cut-off in the band-pass at about 2 Hertz.

To confirm these assumptions, recent studies have been performed using intraretinal and vitreal electroretinogram (ERG) recordings in dark-adapted intact cat retina (Visual Neuroscience, vol. 18(3), pp. 353-363, 2001). These studies compared the changes in the recovery phase following the a- and b-waves induced by an exposure with bright flashes of diffuse white light, after intraretinal injections of substances known to block the responses of bipolar and horizontal cells, or substances known to block $I_h$. The authors of this study have concluded that blockers of $I_h$ reduce the recovery phase following the a-wave induced by the light exposure.

BRIEF DESCRIPTION OF THE DRAWINGS

FIG. 6 shows results of control condition (-■-) and in chronic treatment condition with a single dose of cilobradine of 1 mg/kg body weight given per day during 2 weeks (-603 -).

FIG. 7 shows results in control conditions (-●-) and in chronic treatment conditions with a double dose of zatebradine of 3 mg/kg body weight given per day during 2 weeks (-□-).

SUMMARY OF THE INVENTION

Figure 1:
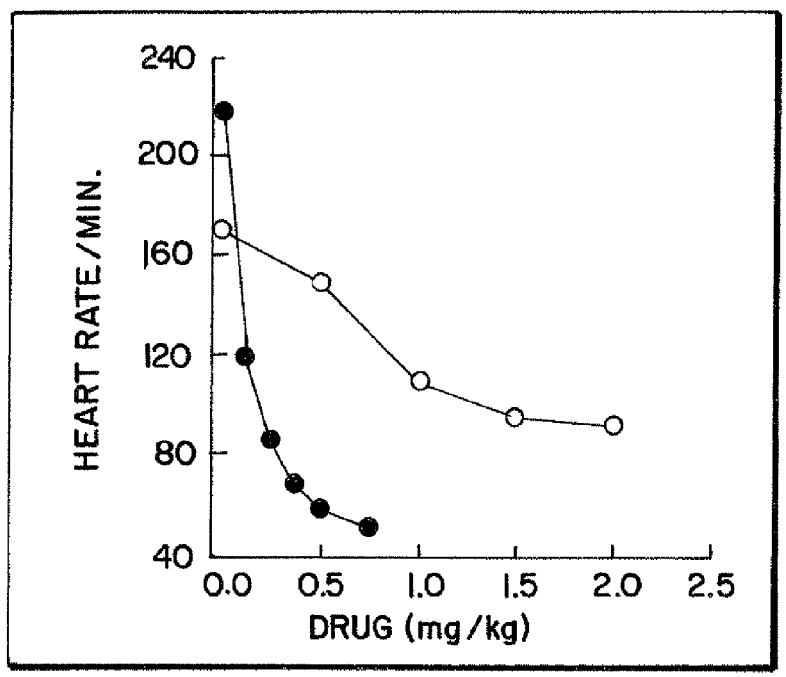
FIG. 1 shows heart rate plotted against the applied dose of zatebradine (-●-) and cilobradine (-○-).

From the results of the recently published scientific studies on the mechanism of action of bradycardic substances, which were discussed in the previous section, one would not expect an advantage of cilobradine over zatebradine in the treatment of cardiac disorders such as heart failure.

However, as shall be discussed below, it has surprisingly been found that cilobradine presents an advantage over zatebradine not only in terms of its pharmacologically longer duration of action and dose potency, but more importantly in its cardioselectivity, resulting in decreased or absent visual side effects when compared to therapeutic doses of zatebradine.

Hence, a first object of the present invention is that cilobradine has intrinsically different pharmacological properties than zatebradine, which permit full cardiac ion channel blockade with absent or diminished retinal effects. This unexpected cardioselective property represents a clear advantage for cilobradine over, for example, zatebradine, for the treatment of cardiac disorders such as heart failure.

A further object of the present invention is that cilobradine is effective for the treatment or prevention of heart failure of any aetiology and thus, is able to reduce the mortality and morbidity associated with heart failure of any aetiology.

Thus, the present invention is directed to the use of cilobradine, or its pharmaceutically acceptable salts, for the treatment or prevention of heart failure of any aetiology.

The present invention is also a method for the treatment or prevention of heart failure of any aetiology, by administration to a patient in need thereof of a pharmaceutical composition comprising cilobradine, or its pharmaceutically acceptable salts, together with a pharmaceutically suitable carrier.

DESCRIPTION OF PREFERRED EMBODIMENTS

In accordance with one embodiment, the present invention provides for a novel use of the cyclic amine derivative (+)-3-[(N-(2-(3,4-dimethoxy-phenyl)-ethyl)-piperidin-3-(S)-yl)-methyl]-7,8-dimethoxy-1,3,4,5-tetrahydro-2H-3-benzazepin-2-one, named cilobradine, or its pharmaceutically acceptable salts.

For the preparation of cilobradine or the pharmaceutically acceptable salts of cilobradine, reference is made to EP 0 224 794 and its US counterpart U.S. Pat. No. 5,175,157, which describes the chemical synthesis of these compounds.

In accordance with a further embodiment of the present invention, amongst the pharmaceutically acceptable salts of cilobradine described in EP 0 224 794 and its US counterpart U.S. Pat. No. 5,175,157, the hydrochloride and hydrobromide salts of cilobradine are preferred.

More particularly, the present invention is directed to the use of cilobradine, or its pharmaceutically acceptable salts, for the preparation of a pharmaceutical composition for the treatment or prevention of heart failure of any aetiology.

In accordance with a further embodiment, the present invention is directed to the use of cilobradine, or its pharmaceutically acceptable salts, for the preparation of a pharmaceutical composition for the prevention of heart failure of any aetiology.

In accordance with a further embodiment of the present invention, the treatment or prevention of heart failure may be assessed by the ability of the compound or pharmaceutical composition in accordance with the present invention to reduce the mortality and morbidity associated with heart failure of any aetiology.

In accordance with a further embodiment of the present invention, the treatment or prevention of heart failure also comprises the treatment or prevention of cardiac insufficiency, cardiac failure, heart insufficiency, myocardial failure, myocardial insufficiency, heart muscle insufficiency, cardiac muscle insufficiency, insufficient cardiac output, heart muscle weakness, cardiac muscle weakness, cardiac collapse, cardiac syncope, chronic heart failure, acute heart failure, heart decompensation, cardiac decompensation, cardial decompensation, diastolic heart failure, right sided heart failure, systolic heart failure, left ventricular heart failure, left sided heart failure, biventricular heart failure and congestive heart failure.

In accordance with a further embodiment of the present invention, heart failure of any aetiology means heart failure diagnosed as a consequence or complication of any other condition, disease or disorder such as, for example, systolic dysfunction, diastolic dysfunction, ischaemic heart diseases, including myocardial infarction, right ventricular infarction and chronic ischaemia, coronary heart diseases, hypertension, primary pulmonary hypertension, secondary pulmonary hypertension, pulmonary embolism, pulmonary arterial stenosis, chronic obstructive pulmonary disease, restrictive cardiomyopathies, dilated cardiomyopathies due to infectious, toxic, metabolic, familial or unknown reasons, myocarditis, congenital anomalies, tachycardias and ventricular hypertrophy secondary to genetic or valvular disorders such as tricuspid valve insufficiency, mitral and/or aortic valve disorders, heart infarcts, thyroid diseases and anaemia.

In accordance with a further embodiment, for the treatment or prevention of heart failure, a combination of cilobradine, or its pharmaceutically acceptable salts, with other substances such as, for example, diuretics, cardiac glycosides, ACE (Angiotensin Converting Enzyme) inhibitors, ARBs (Angiotensin Receptor Blockers), vasodilators, beta blockers and inotropes, present in the same pharmaceutical composition, or given as separate therapies (so-called adjunctive therapy), is also within the scope of the present invention.

In accordance with a further embodiment of the present invention, the pharmaceutical composition for use in accordance with the present invention, comprising cilobradine or its pharmaceutically acceptable salts, alone or in combination with other heart failure therapies including ACE inhibitors, ARBs, diuretics or cardiac glycosides, may be administered to patients in any medically acceptable manner.

In accordance with a further embodiment of the present invention, the pharmaceutical composition for use in accordance with the present invention, comprising cilobradine or its pharmaceutically acceptable salts, may be formulated as liquid formulation or lyophilised powder for oral or parenteral administration. Powders may be reconstituted by addition of a suitable diluent or other pharmaceutically acceptable carrier prior to use. The liquid formulation is generally an aqueous solution. Such formulation is especially suitable for oral administration, but may also be used for parenteral administration or contained in a metered dose inhaler or nebulizer for insufflation. It may be desirable to add excipients such as polyvinylpyrrolidone or hydroxycellulose to the composition.

In accordance with a further embodiment of the present invention, the liquid formulation may be administered directly per orally or filled into a soft capsule.

Alternatively, the ingredients may be encapsulated, tabletted or prepared in a syrup, for oral administration. Pharmaceutically acceptable solid or liquid carriers may be added to enhance or stabilise the composition, or to facilitate the preparation of the composition. The carrier may also include a sustained release material.

In accordance with a further embodiment of the present invention, the pharmaceutical compositions are prepared following the conventional techniques of pharmacy involving milling, mixing, granulating, and compressing, when necessary, for tablet forms, or milling, mixing and filling for capsule forms.

For the preparation of pharmaceutical compositions comprising cilobradine or its pharmaceutically acceptable salts, reference is made in particular to EP 0 224 794 and its US counterpart U.S. Pat. No. 5,175,157 and to WO 01/78699, which describe examples of injectable, oral liquid, tablet, capsule and suppository formulations of cilobradine or its pharmaceutically acceptable salts.

In accordance with a further embodiment of the present invention, the preferred galenical formulation is a tablet or liquid drinking solution, although capsule, suppository and injectable formulations of the active substance cilobradine or its pharmaceutically acceptable salts are also comprised within the scope of the present invention.

In accordance with a further embodiment of the present invention, the pharmaceutical composition comprising the active compound cilobradine or its pharmaceutically acceptable salts can be administered to animals as well as humans.

In accordance with a further embodiment of the present invention, the pharmaceutical composition comprising the active compound cilobradine or its pharmaceutically acceptable salts is preferably administered following a single or multiple stage daily application scheme.

In accordance with a further embodiment of the present invention, when administered for the treatment or prevention of heart failure, preferably a dose of 0.01 to 20 mg/kg body weight of the active substance cilobradine or its pharmaceutically acceptable salts is used, and this in one or more applications per day. Within this range, the following dose ranges are further preferred: 0.05 to 5 mg/kg body weight, 0.1 to 2.5 mg/kg body weight, 0.1 to 1 mg/kg body weight, and 0.1 to 0.75 mg/kg body weight.

The invention will now be described in more detail with reference to the following experiments.

As already mentioned above, previous studies (published in Archives Italiennes de Biologie, vol. 137, pp. 299-309, 1999, and Vision Research, vol. 39, pp. 1767-1774, 1999) have established an experimental animal model to evaluate the side-effects (visual disturbances) seen by patients treated with bradycardic agents, such as zatebradine. The content of these references, and more particularly the experimental parts described therein, are herein incorporated by reference.

These studies were based on a measurement of the electroretinogram (ERG) responses recorded from cat eyes, in normal conditions and after administration of zatebradine.

In the following experiment, the same experiment was performed using cilobradine, and the results compared to the results obtained with zatebradine.

In order to compare the visual side-effect of both compounds in conditions in which the drugs are pharmacologically the most effective in these experiments, as for example in the reduction of heart rate, a dose of 0.75 mg/kg body weight was chosen for cilobradine and a dose of 2.5 mg/kg body weight was chosen for zatebradine. This selection of the dose is based on the result shown in FIG. 1, wherein the reduction of heart rate is plotted against the applied dose of the drug (open circles: zatebradine; filled circles: cilobradine). As can be seen from FIG. 1, at a dose of 2.5 mg/kg body weight, a reduction of about 44% of the heart rate is obtained with zatebradine (maximum effect), and at a dose of 0.75 mg/kg body weight, a reduction of about 75% of the heart rate is obtained with cilobradine (also maximum effect). Therefore, by choosing these doses, it can already be assumed that the pharmacological effect on heart rate of cilobradine is better than the pharmacological effect of zatebradine.

Figure 2:
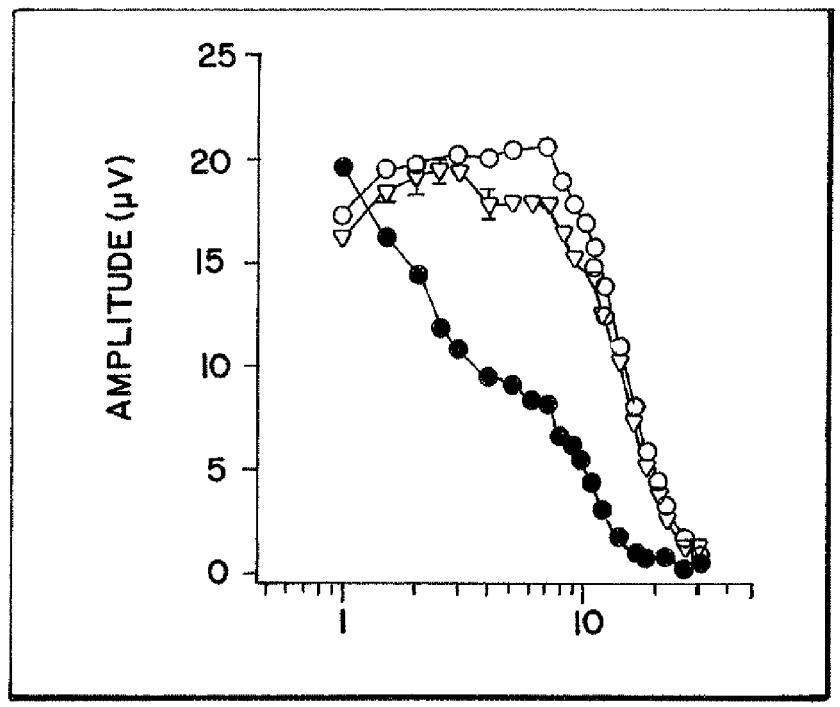
FIG. 2 shows the attenuation and phase characteristics of the ERG response to sinusoidally modulated luminances evaluated by plotting the amplitude of the response to the light stimulus as a function of the temporal frequency of the light stimulus where no active substance was injected (-○-), 15 minutes after treatment (i.v. injection) with a dose of zatebradine of 2.5 mg/kg body weight (-●-), and 5 hours after injection of zatebradine (-▽-).

In a similar experiment than the experiment performed by Gargini et al. (published in Vision Research, vol. 39, pp. 1767-1774, 1999), the attenuation and phase characteristics of the ERG response to sinusoidally modulated luminances was evaluated by plotting the amplitude of the response to the light stimulus as a function of the temporal frequency of the light stimulus. The result of this experiment is shown in FIG. 2, wherein the open circles are the control responses (no active substance injected), the filled circles are the responses 15 minutes after treatment with a dose of zatebradine of 2.5 mg/kg body weight (i.v. injection), and the triangles are the responses measured 5 hours after the injection of zatebradine.

The results confirm the results already published by Gargini et al. (Vision Research, vol. 39, pp. 1767-1774, 1999) that, at this dose, zatebradine reduces the amplitude of the response to stimuli of frequency above 1 Hz and shift the corresponding phase lags, as shown by the ERG recordings. The measurements performed after 5 hours confirm that the visual response is back to normal after 5 hours, and that the experiment is non-destructive for the system.

Figure 3:
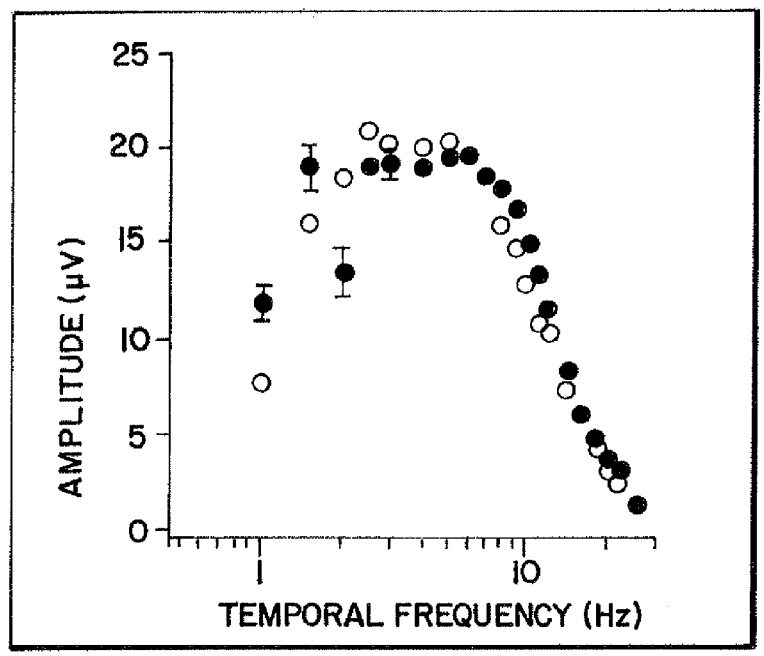
FIG. 3 shows the attenuation and phase characteristics of the ERG response to sinusoidally modulated luminances evaluated by plotting the amplitude of the response to the light stimulus as a function of the temporal frequency of the light stimulus for a control (-○-) and after injection of 0/75 mg/kg weight of cilobradine (-●-).

FIG. 3 shows the results of the same experiment performed after injection of 0.75 mg/kg body weight of cilobradine, in the same conditions. As is clear from the result, no visual effect can be detected with cilobradine when injected in a fully heart rate reduction effective dose.

We conclude from these results that a dose of cilobradine which produces a saturation effect on the heart rate has negligible consequences on the visual response. This evidences the advantage of cilobradine over zatebradine to produce a pharmacological effect with less side-effect, and thus its superiority for the treatment of heart failure.

A further similar experiment was performed in order to compare the visual side-effect of cilobradine and zatebradine in conditions where the drugs are pharmacologically effective in reducing heart rate. The aim of this experiment was to compare the visual side-effect of both drugs in another experimental animal model, namely on the retinal system of the rat. Furthermore, the aim of this experiment was also to compare the visual side-effect of both drugs in acute and in chronic (over two weeks) drug treatment conditions.

The principle of this experiment is again the same as the principle of the experiment performed by Gargini et al. and published in Vision research, vol. 39, pp. 1767-1774, 1999).

Hence, this experiment was based on a measurement of the electroretinogram (ERG) responses recorded from anesthetized pigmented rats as a function of the temporal frequency of an applied oscillating light stimulus. The results of the experiment are visualized by plotting the measurement of the first amplitude of the Fourier transform of the ERG as a function of the applied stimulus frequency (oscillating light stimulus of high luminance and contrast).

FIGS. 4 to 7 show the results of the experiment in different treatment conditions.

Figure 4:
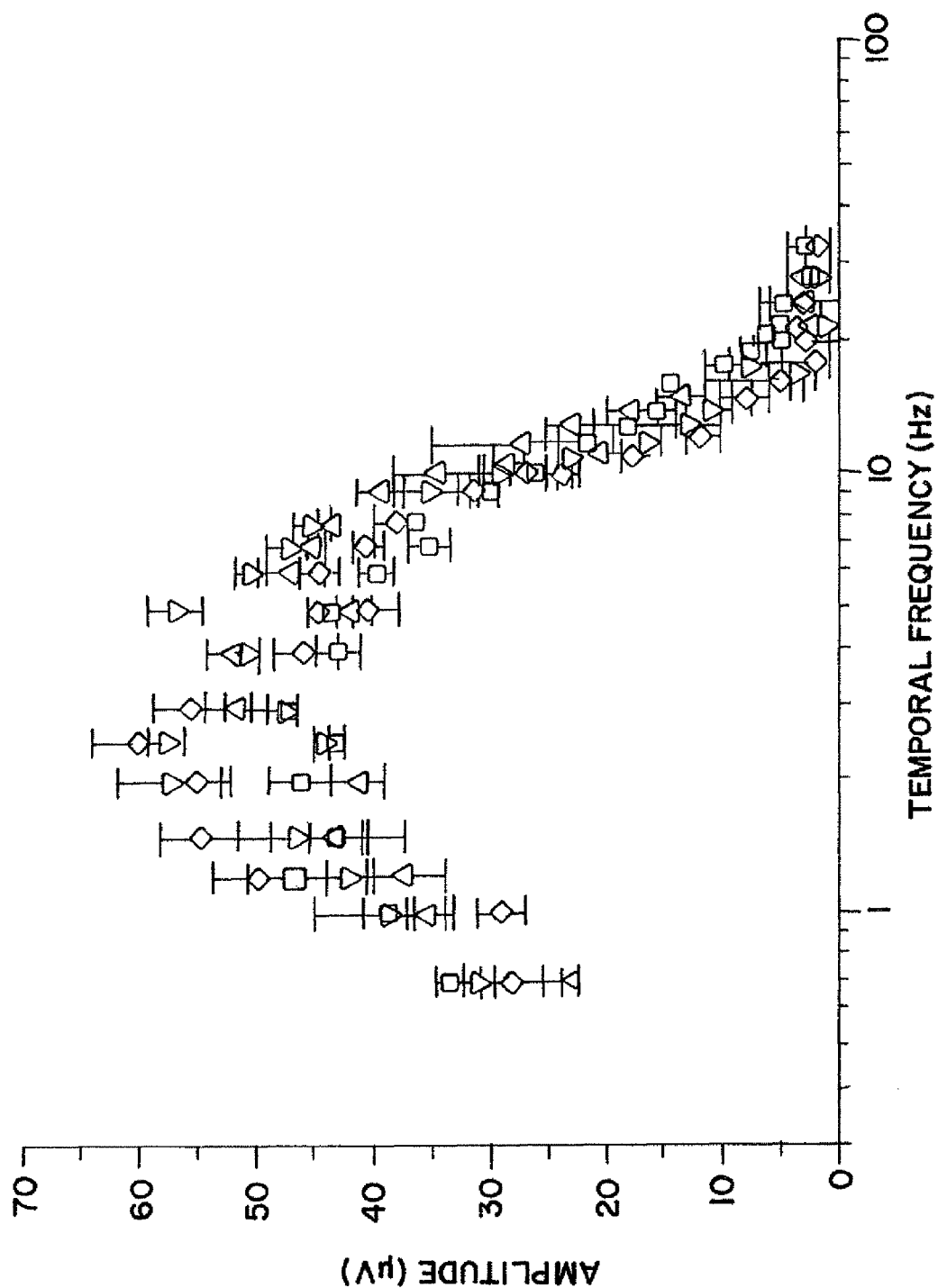
FIG. 4 shows results in control conditions and in acute treatment conditions with three different doses of cilobradine (triangles (-△-): 0.3 mg cilobradine /kg body weight; inverted triangles (-▽-): 1 mg cilobradine /kg body weight; diamonds (-◇-): 3 mg cilobradine /kg body weight: and control; squares (-□-)).

FIG. 4 shows the results of the experiment in control conditions (squares and circles) and in acute treatment conditions with three different doses of cilobradine (triangles: 0.3 mg cilobradine/kg body weight; inverted triangles: 1 mg cilobradine/kg body weight; diamonds: 3 mg cilobradine/kg body weight). The ERG measurements were made 30 minutes after injection of the drug. The measured heart rate frequency was:

| Control | 400 beats per min. |
|---|---|
| Cilobradine treatment 0.3 mg/kg | 364 beats per min. |

-continued

| Cilobradine treatment 1 mg/kg | 316 beats per min. |
|---|---|
| Cilobradine treatment 3 mg/kg | 270 beats per min. |

Figure 5:
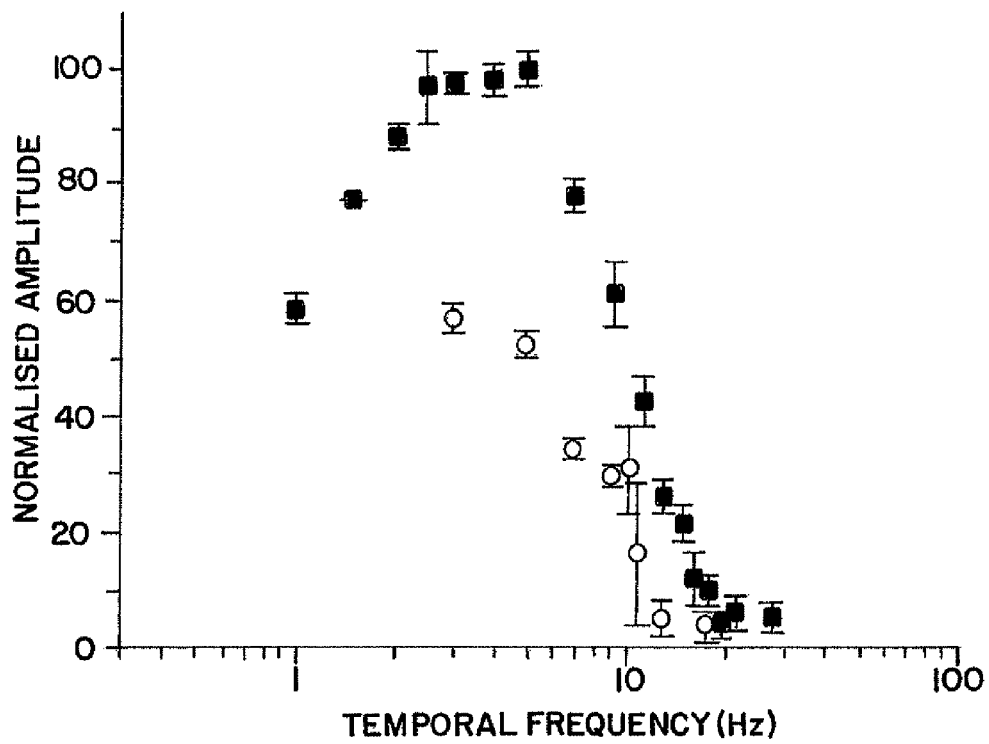
FIG. 5 shows results in control condition (-○-) and in acute treatment condition with a single dose of zatebradine of 3 mg/kg body weight (-■-).

FIG. 5 shows the results of the experiment in control condition (squares and circles) and in acute treatment condition with a single dose of zatebradine of 3 mg/kg body weight (circles). The ERG measurement was made 30 minutes after injection of the drug. The measured heart rate frequency was:

| Control | 428 beats per min. |
|---|---|
| Zatebradine treatment 3 mg/kg | 333 beats per min. |

FIG. 6 shows the results of the experiment in control condition (squares) and in chronic treatment condition with a single dose of cilobradine of 1 mg/kg body weight given per day during 2 weeks (circles). The ERG measurement was made after the 2 weeks treatment. The measured heart rate frequency was:

| Control | 400 beats per min. |
|---|---|
| Cilobradine treatment 1 mg/kg | 260 beats per min. |

FIG. 7 shows the results of the experiment in control conditions (circles) and in chronic treatment conditions with a double dose of zatebradine of 3 mg/kg body weight given per day during 2 weeks (squares). The ERG measurement was made after the 2 weeks treatment. The measured heart rate frequency was:

| Control | 350 beats per min. |
|---|---|
| Cilobradine treatment 1 mg/kg | 285 beats per min. |

From this experiment, it can be concluded that in acute treatment (results of FIGS. 4 and 5), at doses for which both drugs are effective in reducing the heart rate (as confirmed by the values of the measured heart rate frequency), no effect on the ERG can be detected with cilobradine, whereas a reduction of the amplitude of the response to stimuli of frequency above 1 Hz and a shift of the corresponding phase lags is observed with zatebradine.

Furthermore, the same conclusions can be made from the results obtained with chronic treatment over two weeks, as can be seen when comparing the results of FIGS. 6 and 7.

This experiment performed with rats confirms the results previously observed in cats that a dose of cilobradine effective for reducing the heart rate has negligible consequences on the visual response. This also demonstrates again the advantage of cilobradine over zatebradine to produce a pharmacological effect with less side-effect, and thus its superiority for the treatment of heart failure.

This experiment further demonstrates that cilobradine is effective in reducing heart rate without visual side-effects, and thus its suitability in the acute treatment as well as in the chronic treatment of heart failure.

The invention will now also be described in more detail with reference to the following examples of pharmaceutical dosage formulations.

Hence, pharmaceutical formulations for medical use in humans have been prepared containing between 0.10 and 5 mg of active substance. More specifically, oral tablet formulations to be used as single or multiple dose in a daily application scheme, and containing 0.25 mg, 0.5 mg, 1 mg or 2 mg active substance, have been prepared as described in the following formulation examples of film coated tablets.

|  | Example 1<br>0.25 mg Dosis<br>mg/Film<br>Coated Tablet | Example 2<br>0.5 mg Dosis<br>mg/Film<br>Coated Tablet | Example 3<br>1 mg Dosis<br>mg/Film<br>Coated Tablet | Example 4<br>2 mg Dosis<br>mg/Film<br>Coated Tablet |
|---|---|---|---|---|
| Core: | | | | |
| Cilobradine | 0.27 | 0.54 | 1.08 | 2.16 |
| Lactose Monohydrat (Tablettose) | 56.42 | 56.15 | 82.28 | 164.56 |
| Microcrystalline Cellulose, Type 101 | 27.45 | 27.45 | 40.38 | 80.76 |
| Na-Carboxymethylcellulose (Ac-Di-Sol) | 0.43 | 0.43 | 0.63 | 1.26 |
| Magnesiumstearate, (vegetal origin) | 0.43 | 0.43 | 0.63 | 1.26 |
| Weight of Tablet Core: | 85.00 | 85.00 | 125.00 | 250.00 |
| Coating: | | | | |
| Hypromellose (Methocel E5 Premium) | 1.50 | 1.50 | 2.00 | 3.00 |
| Macrogol 400 | 0.15 | 0.15 | 0.20 | 0.30 |
| Titaniumdioxide | 0.75 | 0.75 | 1.00 | 1.50 |
| Talkum | 0.60 | 0.60 | 0.80 | 1.20 |
| Weight of Film Coated Tablet: | 88.00 | 88.00 | 129.00 | 256.00 |

These tablets may be used for the treatment or prevention of heart failure as defined in the present invention.

What is claimed is:

1. A method of treating systolic heart failure or diastolic heart failure, said method comprising:
    selecting a pharmaceutical composition that, when administered to a patient, is known to not produce any significant effect in retinal side effects of the patient as measured by an electroretinogram (ERG) response of the patient to a sinusoidally modulated light stimuli, wherein the pharmaceutical composition comprises a therapeutically effective amount of cilobradine or a pharmaceutically acceptable salt thereof, together with a pharmaceutically suitable carrier, the therapeutically effective amount being between 0.05 and 5 mg/kg body weight; and
    administering to the patient the pharmaceutical composition.

2. The method of claim 1, wherein the patient having insufficient cardiac output has systolic heart failure.

3. The method of claim 1, wherein the patient having insufficient cardiac output has diastolic heart failure.

4. The method of claim 1, wherein the pharmaceutical composition is administered daily for a period of at least two weeks.

5. The method of claim 1, wherein the galenical formulation of the pharmaceutical composition is selected from a tablet, a drinking solution, a capsule, a suppository or an injectable formulation.

6. The method of claim 5, wherein the galenical formulation of the pharmaceutical composition is a tablet.

7. The method of claim 5, wherein the galenical formulation of the pharmaceutical composition is a drinking solution.

8. The method of claim 1, wherein the pharmaceutical composition is administered daily.

9. The method of claim 8, wherein the therapeutically effective amount is between 0.1 and 2.5 mg/kg body weight.

10. The method of claim 8, wherein the therapeutically effective amount is between 0.1 and 1 mg/kg body weight.

11. The method of claim 8, wherein the therapeutically effective amount is between 0.1 and 0.75 mg/kg body weight.

12. The method of claim 1, wherein the pharmaceutical composition is administering in combination with diuretics, cardiac glycosides, Angiotension Converting Enzyme (ACE) inhibitors, Angiotensin II Receptor blockers (ARBs), vasodilators, beta-blockers, or inotropes.

* * * * *